(12) United States Patent
Booker et al.

(10) Patent No.: US 11,119,043 B2
(45) Date of Patent: Sep. 14, 2021

(54) ANALYZER

(71) Applicant: PROCISEDX INC., San Diego, CA (US)

(72) Inventors: David Booker, San Diego, CA (US); Michael Hale, San Diego, CA (US); Raj Srikrishnan, San Diego, CA (US); Mark Mayernick, Boulder, CO (US); Xiaopei Huang, Boulder, CO (US)

(73) Assignee: PROCISEDX INC., San Diego (CA)

( * ) Notice: Subject to any disclaimer, the term of this patent is extended or adjusted under 35 U.S.C. 154(b) by 0 days.

(21) Appl. No.: 16/835,170

(22) Filed: Mar. 30, 2020

(65) Prior Publication Data
US 2020/0225158 A1    Jul. 16, 2020

Related U.S. Application Data

(63) Continuation of application No. PCT/IB2019/051213, filed on Feb. 14, 2019.

(60) Provisional application No. 62/631,165, filed on Feb. 15, 2018.

(51) Int. Cl.
*G01N 21/64* (2006.01)
*G01N 33/49* (2006.01)

(52) U.S. Cl.
CPC ..... *G01N 21/6428* (2013.01); *G01N 21/6486* (2013.01); *G01N 33/49* (2013.01)

(58) Field of Classification Search
CPC .......... G01N 21/6428; G01N 21/6486; G01N 33/49; G01N 2021/1736; G01N 2021/174; G01N 2021/6471; G01N 21/645
See application file for complete search history.

(56) References Cited

U.S. PATENT DOCUMENTS

| | | | | |
|---|---|---|---|---|
| 5,077,480 A | * | 12/1991 | Traina ............... | G01N 21/534 250/575 |
| 5,194,916 A | * | 3/1993 | Hayashi ............. | G01J 3/4406 250/458.1 |
| 10,274,428 B2 | * | 4/2019 | Ehring ............... | G01N 21/645 |
| 2002/0045272 A1 | * | 4/2002 | McDevitt ........... | C12Q 1/37 436/518 |
| 2005/0231966 A1 | * | 10/2005 | Ostler ............... | G01N 21/6447 362/458 |

(Continued)

FOREIGN PATENT DOCUMENTS

| | | |
|---|---|---|
| WO | WO 2011/120006 A1 | 9/2011 |
| WO | WO 2016/083416 A1 | 6/2016 |

OTHER PUBLICATIONS

European Patent Office; International Search Report of PCT/IB2019/051213, dated May 16, 2019.

*Primary Examiner* — Kiho Kim
(74) *Attorney, Agent, or Firm* — Kilpatrick Townsend & Stockton LLP

(57) ABSTRACT

Provided herein are analyzers as well as related methods for measuring both an absorbance and emission of a sample. The analyzer includes light sources for epi-illumination and transillumination of the sample, and detectors for measuring the intensities of excitation, emission, and transillumination light. A dichroic mirror permits a portion of the excitation light to transmit to a detector that monitors changes in excitation light intensity. Temperature sensors allow for signal corrections based on temperature variations of the detectors and sample.

33 Claims, 11 Drawing Sheets

(56) References Cited

U.S. PATENT DOCUMENTS

| | | | |
|---|---|---|---|
| 2006/0041385 A1* | 2/2006 | Bauer | G01N 1/30 702/19 |
| 2007/0035819 A1* | 2/2007 | Bahatt | G01J 3/10 359/366 |
| 2011/0226962 A1* | 9/2011 | Boudreau | G02B 21/16 250/459.1 |
| 2012/0031577 A1* | 2/2012 | Banks | D21H 21/30 162/198 |
| 2013/0210067 A1* | 8/2013 | Chandrapati | C12Q 1/04 435/34 |
| 2014/0296666 A1* | 10/2014 | Rabinovitz | A61B 5/0084 600/310 |
| 2015/0090900 A1* | 4/2015 | Banks | G01N 21/645 250/432 R |
| 2018/0328835 A1* | 11/2018 | Bauer | A61B 5/14532 |

\* cited by examiner

ANALYZER

CROSS-REFERENCES TO RELATED APPLICATIONS

This application is a continuation of PCT Application No. PCT/IB2019/051213, filed Feb. 14, 2019, which application claims the benefit of U.S. Provisional Patent Application No. 62/631,165, filed Feb. 15, 2018, which applications are incorporated by reference in their entireties for all purposes.

BACKGROUND

Light absorbance is a commonly used analytical technique for determining the composition of a liquid sample. For example, the absorbance of light having a wavelength of 450 nm or 600 nm is commonly used as a turbidity measurement indicative of, for example, cell growth in a culture medium. Colorimetric light absorbance assays can be an effective tool for tracking the conversion of reactions in which one or more reactants or products have chromophoric properties. The concentration of proteins in a solution can be measured by determining the absorbance by the solution of light having a wavelength of 280 nm, as this ultraviolet light is strongly absorbed by the aromatic side chains of proteinaceous amino acids.

Other analytical techniques monitor the light that is emitted, rather than absorbed, by a sample and its components. The wide variety and high sensitivity of available fluorophores as labels, tags, and indicators, have provided a motivation for the development of a large number of well-studied fluorescence assays. As one example, fluorescence resonance energy transfer (FRET) assays involve a process in which a donor molecule (e.g., a cryptate dye) absorbs light, entering an excited state. Rather than emitting light, the first molecule transfers its excited state to an acceptor molecule with other properties (e.g., a dye fluorescing at a different wavelength or a quencher), and the acceptor fluoresces or quenches the excitation. Because the efficiency of the transfer is dependent on the proximity of the two molecules, the signal can provide information about molecular complex formation or biomolecular structure.

While both light absorbance and fluorescence have been well demonstrated as being important tools for analytical chemistry and biology, the simultaneous application of both of these approaches poses some challenges. For example, some fluorophores and colored compounds can interfere with another, reducing the sensitivities of measurements of their presence. Also, the different optical equipment used to perform the detection of fluorescence and absorbance typically necessitates some degree of operator interaction in switching from one assay modality to another. In view of the foregoing, the need exists for an analyzer that can be used to easily and accurately measure the fluorescence and absorbance of the same sample. The presently disclosed devices and methods provide solutions to these and other needs.

BRIEF SUMMARY

One provided apparatus for detecting an emission light from a sample, and absorbance of a transillumination light by the sample, comprises a first light source configured to emit an excitation light having an excitation wavelength. The apparatus further comprises a second light source configured to transilluminate the sample with the transillumination light. The apparatus further comprises a first light detector configured to detect the excitation light, and a second light detector configured to detect the emission light and the transillumination light. The apparatus further comprises a dichroic mirror configured to (1) epi-illuminate the sample by reflecting at least a portion of the excitation light, (2) transmit at least a portion of the excitation light to the first light detector, (3) transmit at least a portion of the emission light to the second light detector, and (4) transmit at least a portion of the transillumination light to the second light detector.

In some embodiments, the apparatus further comprises an emission temperature sensor configured to detect the temperature of the second light detector. In some embodiments, the apparatus further comprises an excitation temperature sensor configured to detect the temperature of the first light detector. In some embodiments, the apparatus further comprises a sample temperature sensor configured to detect the temperature of the sample. In some embodiments, the sample temperature sensor is located substantially orthogonal to a line comprising the sample and a portion of the dichroic mirror.

In some embodiments, the dichroic mirror is configured at substantially a 45-degree angle relative to a line comprising the sample and a portion of the first light source. In some embodiments, the dichroic mirror is configured to reflect at least a portion of the excitation light from the first light source at substantially a 90-degree angle. In some embodiments, the apparatus further comprises an excitation objective lens between the dichroic mirror and a sample contained within a cuvette. In some embodiments, the excitation objective lens is configured to focus the excitation light onto the sample.

In some embodiments, the apparatus further comprises a band pass filter disposed between the second light detector and the dichroic mirror. In some embodiments, the band pass filter allows only visible light having a wavelength ranging from about 390 nm to about 700 nm to pass to the second light detector. In some embodiments, the emission light transmitted through the dichroic mirror passes through the band pass filter and is focused on the second light detector. In some embodiments, the transillumination light transmitted through the dichroic mirror passes through the band pass filter and is focused on the second light detector. In some embodiments, the apparatus further comprises a filter wheel holding the band pass filter. In some embodiments, the band pass filter is a first band pass filter, and the filter wheel further holds one or more additional band pass filters.

In some embodiments, the second light detector is a photomultiplier detector, such as a silicon photomultiplier. In some embodiments, the first light detector is a photodiode. In some embodiments, the excitation light has a wavelength within the ultraviolet wavelength range. In some embodiments, the transillumination light has a wavelength within the visible wavelength range. In some embodiments, the second light source comprises a first light emitting diode (LED) configured to emit a first light (e.g., visible red light), and a second LED configured to emit a second light (e.g., visible green light). In some embodiments, the second light source comprises more than two light emitting diodes. In certain aspects, each one of the more than two light emitting diodes has a different dominant wavelength than that of the other of the more than two light emitting diodes. In some embodiments, at least one of the first light source and the second light source comprises a cap with ribs configured to dissipate heat. In some embodiments, the apparatus is configured to detect or measure a sample contained within a cuvette. In some embodiments, the sample comprises a biological sample such as whole blood, plasma, serum, red blood cells, or white blood cells.

In some embodiments, the apparatus further comprises a barcode reader. In some embodiments, the barcode reader is within the instrument housing. In some embodiments, the barcode reader is external to the instrument housing. In some embodiments, the apparatus further comprises a printer module within the instrument housing. In some embodiments, the apparatus further comprises a touchscreen mounted to an external surface of the housing.

Also provided are methods for detecting an emission light from a sample, and absorbance of transillumination light by the sample. The method comprises providing the apparatus of any of the provided embodiments described above. The method further comprises inserting the sample within a cuvette into the apparatus. The method further comprises epi-illuminating the sample using the first light source. The method further comprises detecting excitation light transmitted through the dichroic mirror using the first detector. The method further comprises detecting emission light transmitted from the sample through the dichroic mirror using the second detector. The method further comprises transilluminating the sample using the second light source to generate a transillumination light. The method further comprises detecting the transillumination light transmitted through the dichroic mirror with the second detector to thereby detect the emission light from the sample and the absorbance of transillumination light by the sample.

In some embodiments, the method further comprises measuring a dark current with the second detector, prior to inserting the sample into the apparatus. In some embodiments, the method further comprises adjusting an amount of excitation light emitted by the first light source based on the excitation light monitored using the first detector. In some embodiments, the method further comprises measuring an inherent fluorescence of the sample, using, for example, the second detector after the epi-illuminating. In some embodiments, the method further comprises measuring a blank absorbance with the second light detector prior to inserting the sample into the apparatus In some embodiments, the apparatus further comprises an emission temperature sensor configured to detect the temperature of the second light detector, and the method further comprises correcting a signal output by the second light detector based on the temperature detected using the emission temperature sensor. In some embodiments, the apparatus further comprises an excitation temperature sensor configured to detect the temperature of the first light detector, and the method further comprises correcting a signal output by the first light detector based on the temperature detected using the excitation temperature sensor.

Also provided are systems for detecting an emission light from a sample, and absorbance of transillumination light by the sample. The system comprises the apparatus of any of the provided embodiments described above. The system further comprises at least one processor. The system further comprises a memory operatively coupled with the at least one processor, the at least one processor executing instructions from the memory. The instructions comprise program code for epi-illuminating the sample using the first light source. The instructions further comprise program code for detecting excitation light transmitted through the dichroic mirror using the first detector. The instructions further comprise program code for detecting emission light transmitted from the sample through the dichroic mirror using the second detector. The instructions further comprise program code for transilluminating the sample using the second light source to generate the transillumination light. The instructions further comprise program code for detecting the transillumination light transmitted through the dichroic mirror with the second detector to thereby detect the absorbance of transillumination light by the sample.

In some embodiments, the instructions further comprise program code for measuring a dark current with the second detector, prior to inserting the sample into the apparatus. In some embodiments, the instructions further comprise program code for adjusting an amount of excitation light emitted by the first light source based on the excitation light monitored using the first detector. In some embodiments, the instructions further comprise program code for measuring an inherent fluorescence of the sample, using, for example, the second detector after the epi-illuminating. In some embodiments, the instructions further comprise program code for measuring a blank absorbance with the second light detector prior to inserting the sample into the apparatus In some embodiments, the apparatus further comprises an emission temperature sensor configured to detect the temperature of the second light detector, and the instructions further comprise program code for correcting a signal output by the second light detector based on the temperature detected using the emission temperature sensor. In some embodiments, the apparatus further comprises an excitation temperature sensor configured to detect the temperature of the first light detector, and the instructions further comprise program code for correcting a signal output by the first light detector based on the temperature detected using the excitation temperature sensor. These and other objects, aspects and embodiments will become more apparent when read with the detailed description and figures which follow.

DETAILED DESCRIPTION

Figure 1A:
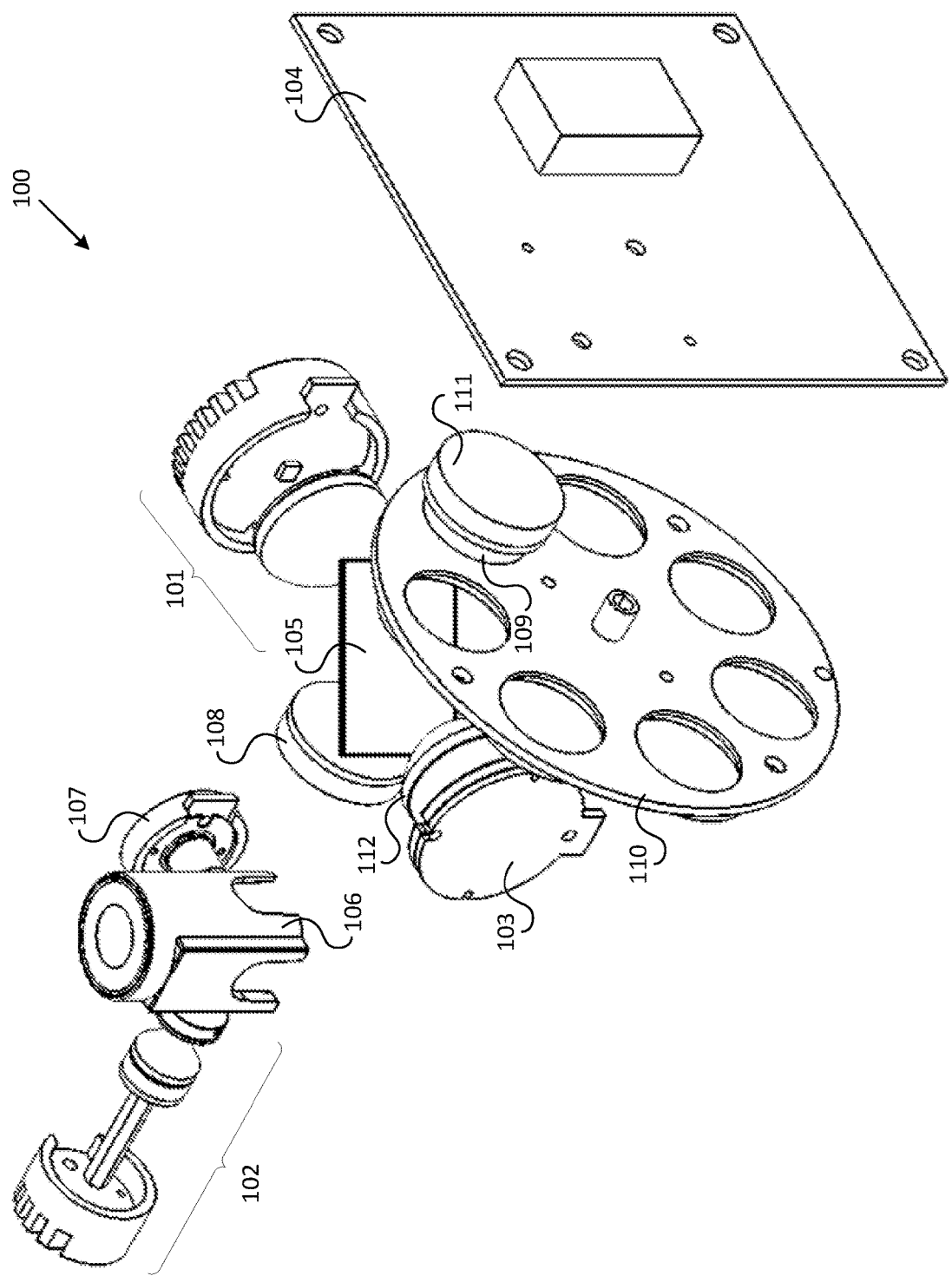
FIG. 1A is an illustration of an isometric view of selected components of an analyzer in accordance with an embodiment.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other scientific terms or terminology used herein have the same meaning as is commonly understood by one of ordinary skill in the art to which this disclosure belongs. As appropriate, procedures involving the use of commercially available kits and reagents are generally carried out in accordance with manufacturer defined protocols and/or parameters unless otherwise noted.

The present disclosure generally relates to analyzers that can be used in point-of-care settings to measure the absorbance and fluorescence of a sample with minimal or no user handling or interaction. These analyzers provide advantageous features of more rapid and reliable analyses of samples having properties that can be detected with each of these two approaches. For example, it can be beneficial to quantify both the fluorescence and absorbance of a blood sample being subjected to a diagnostic assay. In some analytical workflows, the hematocrit of a blood sample can be quantified with an absorbance assay, while the signal intensities measured in a FRET assay can provide information regarding other components of the blood sample. It has been difficult, however, to perform such different assay methods within the same instrument when using conventional and readily available analyzers. This has been the case, for example, because the optical elements, electrical requirements, or instrument configurations required for one assay method may be ineffective or incompatible with the operation of an another assay. As a result of these differences, operators of typical analyzers often must use separate instruments to perform separate assays, or must manually adjust a sample or instrument in transitioning from one assay procedure to another.

The inventors have now discovered that through a particular set of configurations of optical and electronic elements, an analyzer is capable of measuring both fluorescence and absorbance for the same sample using a single instrument, such as a compact benchtop or point-of-care instrument. In such configurations, there is little to no requirement for user interaction. The provided analyzers include light sources and detectors used to illuminate a sample with excitation light and transillumination light, and to measure the resulting emission light and absorbance light intensities. The beam splitters, mirrors, and/or lenses of the analyzer direct different beams of light to and through the sample in such a way that switching between the two detection modalities can be easily and automatically accomplished.

Furthermore, by configuring the optical system of the analyzer such that some of the excitation light of the analyzer is diverted to a secondary detector, rather than directed to the illumination of a sample, this detector can be used as a power meter measuring excitation light intensity. By monitoring changes in excitation light in this fashion, adjustments can be made to the optical system to better restore and maintain constant excitation light output. Such constant excitation can be critical for highly precise fluorescence measurements.

Another advantage offered by the provided analyzer and related methods is the inclusion of independent temperature sensors, with some exemplary embodiments including a plurality of independent temperature sensors such as 2, 3 or more temperature sensors. These sensors allow measurements of various temperature-sensitive analyzer elements to be monitored, and related compensation actions to be performed in response to temperature variations. For example, by enabling the simultaneous detection of the temperatures of each of two light detectors in a system, as well as the sample being analyzed, more robust corrections to assay signal outputs can be made, and the accuracy and precision of the analyzer can be increased.

I. Analyzers

Figure 1B:
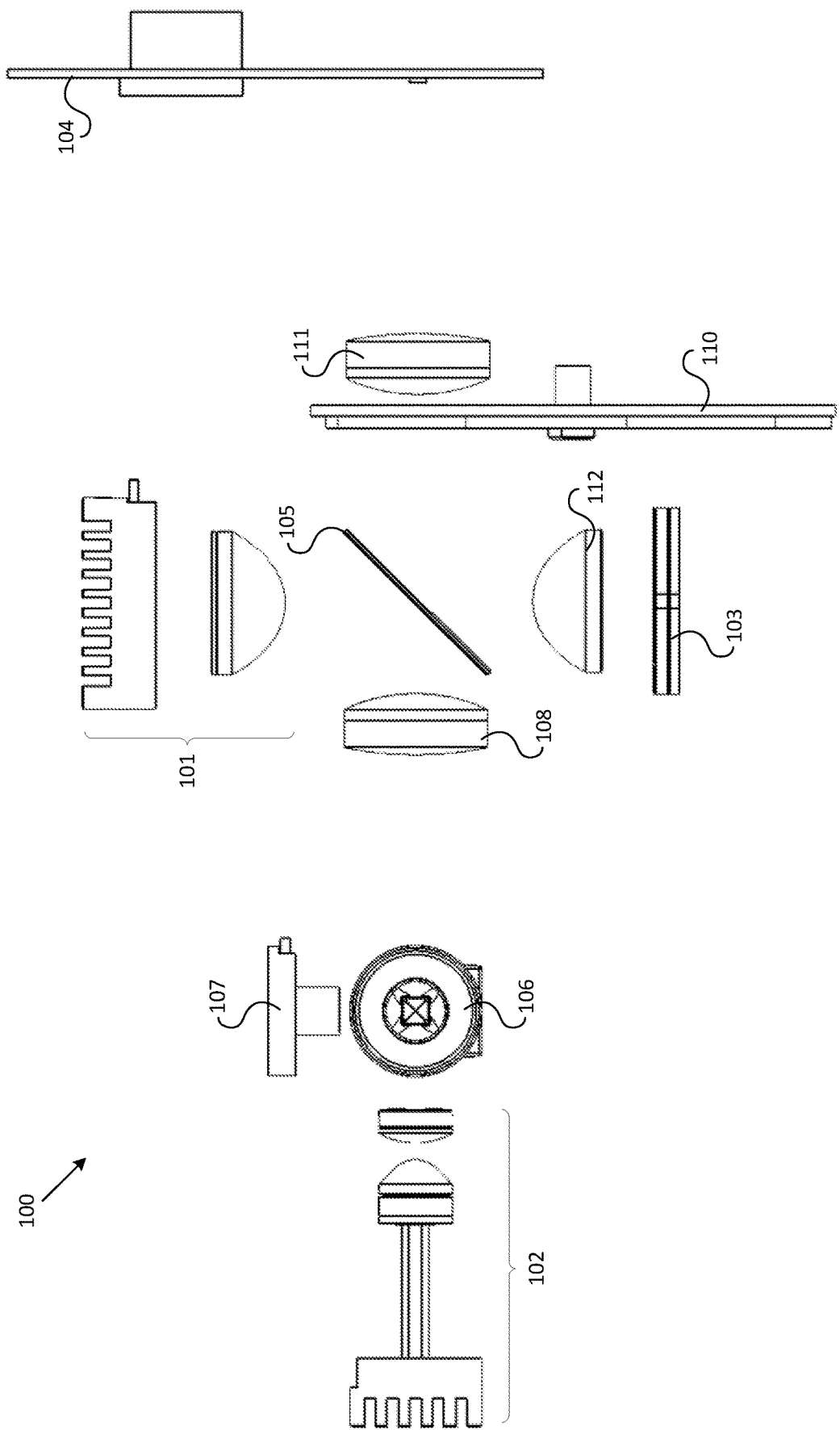
FIG. 1B is an illustration of a top view of the analyzer components of FIG. 1A.

FIGS. 1A and 1B illustrate selected components of an exemplary analyzer for detecting and or measuring an emission light from a sample, and absorbance of a transillumination light by the sample, in accordance with an embodiment. The view in FIG. 1A is of the analyzer components from an isometric viewpoint, and the view in FIG. 1B is of the same analyzer components from a top-down viewpoint. Shown in the figures is an analyzer (100) that includes a first light source (101) that is configured to emit an excitation light. The analyzer (100) also includes a second light source (102) configured to emit a transillumination light. A first light detector (103) is configured to detect the excitation light produced by the first light source (101), and a second light detector (104) is configured to detect the transillumination light produced by the second light source (102). The second light detector (104) is also configured to detect emission light emitting from a sample within a cuvette (106), for example, in response to the excitation light produced by the first light source (101).

As illustrated, a dichroic mirror (105) can be centrally located within the analyzer (100), and used to direct and split different light beams therein. The dichroic mirror (105) can be configured to epi-illuminate the sample within a cuvette (106) by reflecting at least a portion of the excitation light produced by the first light source (101). The dichroic mirror (105) can also be configured to transmit at least a portion of the excitation light to the first light detector (103). The dichroic mirror (105) can also be configured to transmit at least a portion of the emission light originating from the sample within a cuvette (106) to the second light detector (104). The dichroic mirror (105) can also be configured to transmit at least a portion of the transillumination light to the second light detector (104). In some embodiments, and as shown in FIGS. 1A and 1B, the first light source (101) and first light detector (103) are oriented horizontally with respect to the second light source (102), the second light detector (104), and the cuvette (106). In some embodiments, and as shown in FIG. 5C, the first light source (101) and first light detector (103) are oriented vertically with respect to the second light source (102), the second light detector (104), and the cuvette.

The analyzer of FIGS. 1A-1E also includes a sample temperature sensor (107) that is configured to detect the temperature of a sample within a cuvette (106). The sample temperature sensor (107) is generally located substantially orthogonal to a line connecting the sample and a portion of the dichroic mirror. In this way, the sample temperature sensor (107) is also substantially orthogonal to the path of the excitation, emission, and transillumination light beams passing through or originating within a sample within a cuvette (106). This allows the sample temperature sensor (107) to function to measure the temperature of the sample within a cuvette (106) without interfering with the functions of the optical components of the analyzer (100). It is appreciated that the sample temperature sensor can be positioned in other locations within an analyzer so long as the sample temperature sensor does not substantially obstruct the path of the excitation, emission, and transillumination light beams.

An excitation objective lens (108) is positioned between the dichroic mirror (105) and the sample within a cuvette (106). As excitation light originating from the first light source (101) travels through the excitation objective lens (108), the excitation light is focused onto the cuvette (106) and the sample contained within the cuvette (106). A band pass filter (109) is positioned between the dichroic mirror (105) and the second light detector (104). As emission light originating from the sample within a cuvette (106) travels through the band pass filter (109), the emission light is filtered to remove wavelengths outside of a specific wavelength range. In some embodiments, and as is shown in FIGS. 1A-1E, the band pass filter (109) is an element of a filter wheel (110) that holds the band pass filter(s) (109). The filter wheel optionally holds a plurality of band pass filters.

Also included in the analyzer (100) are a first detector objective lens (112) positioned between the dichroic mirror (105) and the first light detector (103), and a second detector objective lens (111) positioned between the dichroic mirror (105) and the second light detector (104). The first (112) and second (111) detector objective lenses act to focus light on the first (103) and second (104) light detectors, respectively.

Figure 1C:
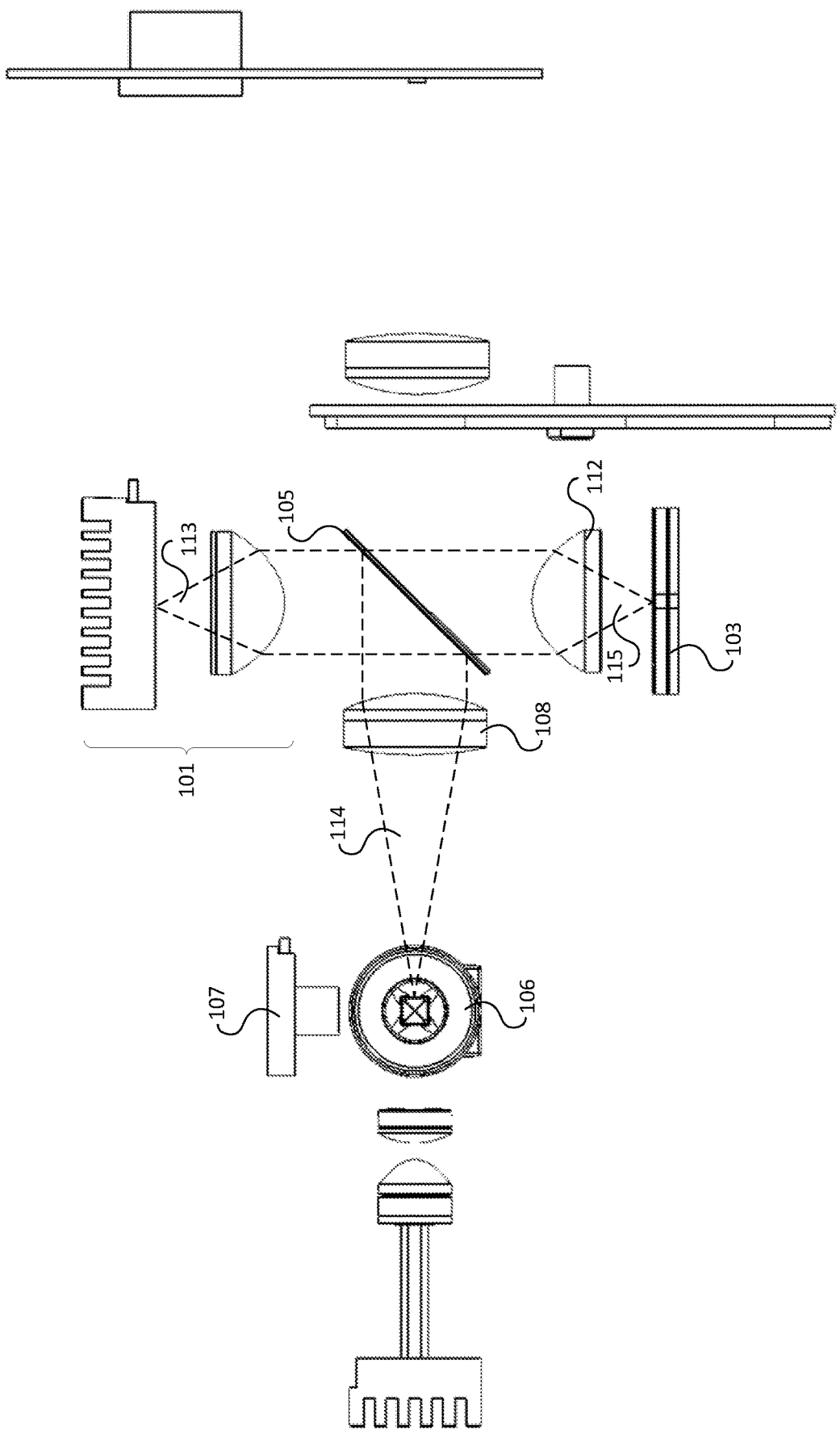
FIG. 1C is an illustration of the analyzer of FIG. 1B depicting the epi-illumination of a sample with excitation light.

FIG. 1C illustrates a simplified overhead view of the analyzer (100) of FIGS. 1A and 1B when being used to epi-illuminate the sample within the cuvette (106). As shown in FIG. 1C, the first light source (101) generates an excitation light (113) that is directed towards the dichroic mirror (105). The dichroic mirror reflects a major portion of the excitation light (113) at a substantially 90-degree angle, directing the reflected beam (114) towards the sample within the cuvette (106). As the reflected excitation light (114) passes through the excitation objective lens (108), the excitation objective lens (108) focuses the reflected excitation light (114) onto the sample within the cuvette (106). A minor portion of the excitation light (115) from the first light source (101) is transmitted through the dichroic mirror (105). This transmitted excitation light (115) passes through the first detector objective lens (112), which focuses the transmitted excitation light (115) onto the first light detector (103).

Figure 1D:
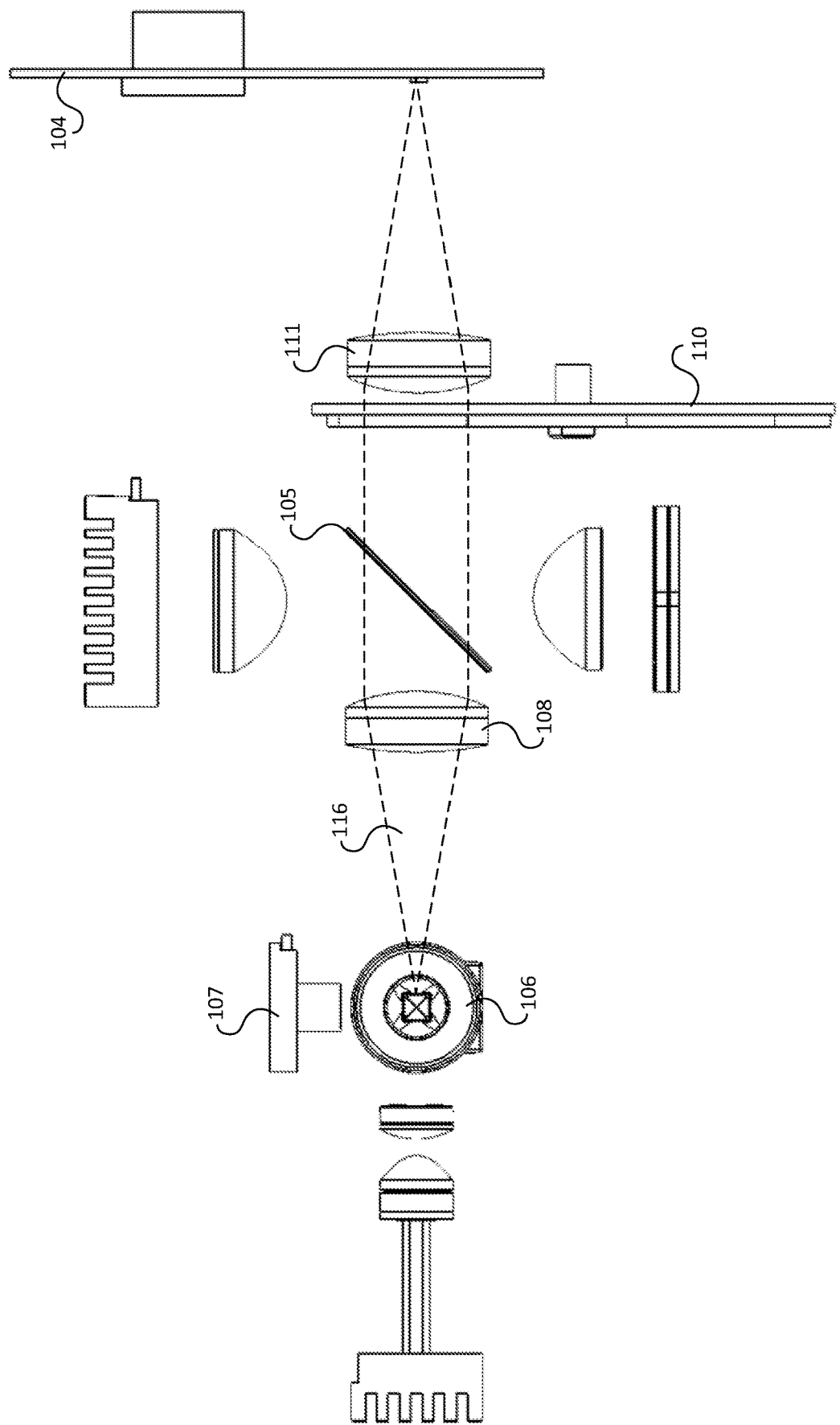
FIG. 1D is an illustration of the analyzer of FIG. 1B depicting the emission light originating from the sample.

FIG. 1D illustrates a simplified overhead view of the analyzer (100) of FIGS. 1A and 1B upon excitation of the sample within the cuvette (106) by epi-illumination with excitation light as in FIG. 1C. Upon excitation, the sample within the cuvette (106) emits an emission light (116) that is collimated as it passes through the excitation objective lens (108) in a direction towards the dichroic mirror (105). The emission light (116) is transmitted through the dichroic mirror (105) and a band pass filter of the filter wheel (110). As the emission light (116) then passes through the second detector objective lens (111), the emission light (116) is focused onto the second light detector (104). While FIGS. 1C and 1D illustrate the excitation and emission of the sample separately, it is appreciated that excitation and emission can, and in certain embodiments typically do, occur substantially simultaneously.

Figure 1E:
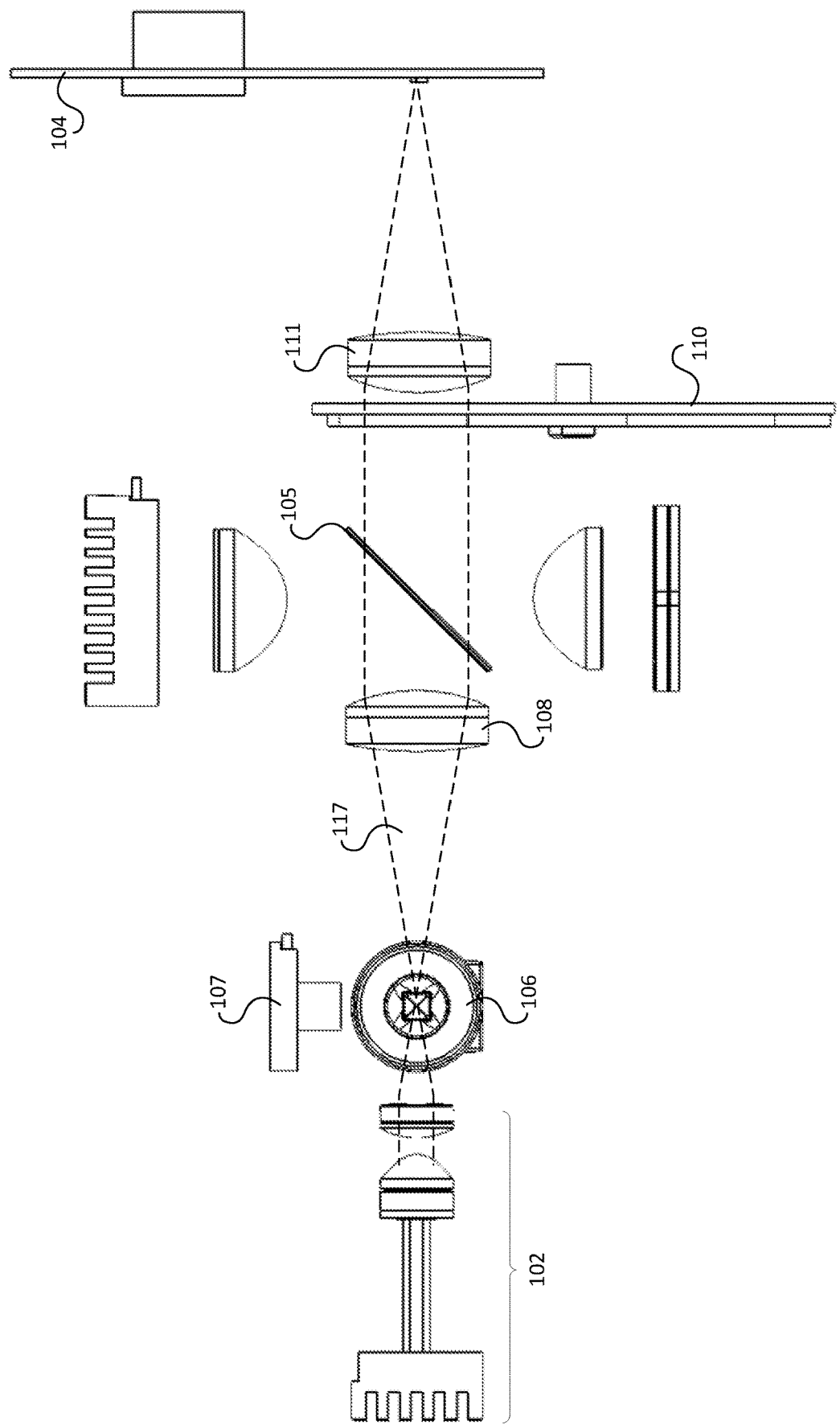
FIG. 1E is an illustration of the analyzer of FIG. 1B depicting the transillumination of the sample with transillumination light.

FIG. 1E illustrates a simplified overhead view of the analyzer (100) of FIGS. 1A and 1B when being used to transilluminate the sample (106). As shown in FIG. 1E, the second light source (102) generates a transillumination light (117) that is directed towards the sample (106). The transillumination light (117) that is not absorbed by the sample (106) then travels to the excitation light objective lens (108), which collimates the transillumination light (117) traveling in a direction towards the dichroic mirror (105). The transillumination light (117) is transmitted through the dichroic mirror (105) and a band pass filter of the filter wheel (110). As the transmission light (dashed lines) (117) then passes through the second detector objective lens (111), the transmission light (117) is focused onto the second light detector (104).

In any of the embodiments described herein, including those illustrated in FIGS. 1A-1E, the dichroic mirror of the analyzer can be replaced with, for example, a beam splitter. The beam splitter can reflect approximately 50% of all light, independent of wavelength, and transmit approximately 50% of all light, also independent of wavelength. The independence of the beam splitter with respect to light wavelengths can permit the analyzer to be operated with a greater flexibility with respect to excitation, emission, and transillumination lights. Alternatively, the use of a dichroic mirror instead of a beam splitter can permit the analyzer to operate with a greater degree of sensitivity with respect to a particular excitation, emission, and transillumination wavelengths of interest. In any of the embodiment described herein, the dichroic mirror or beam splitter can be replaced with a piece of non-ultraviolet coated glass. Due to the lack of ultraviolet coating, this type of glass can be used to reflect, for example, approximately 8% of ultraviolet light, while transmitting the remainder of light impinging upon the glass.

Figure 2:
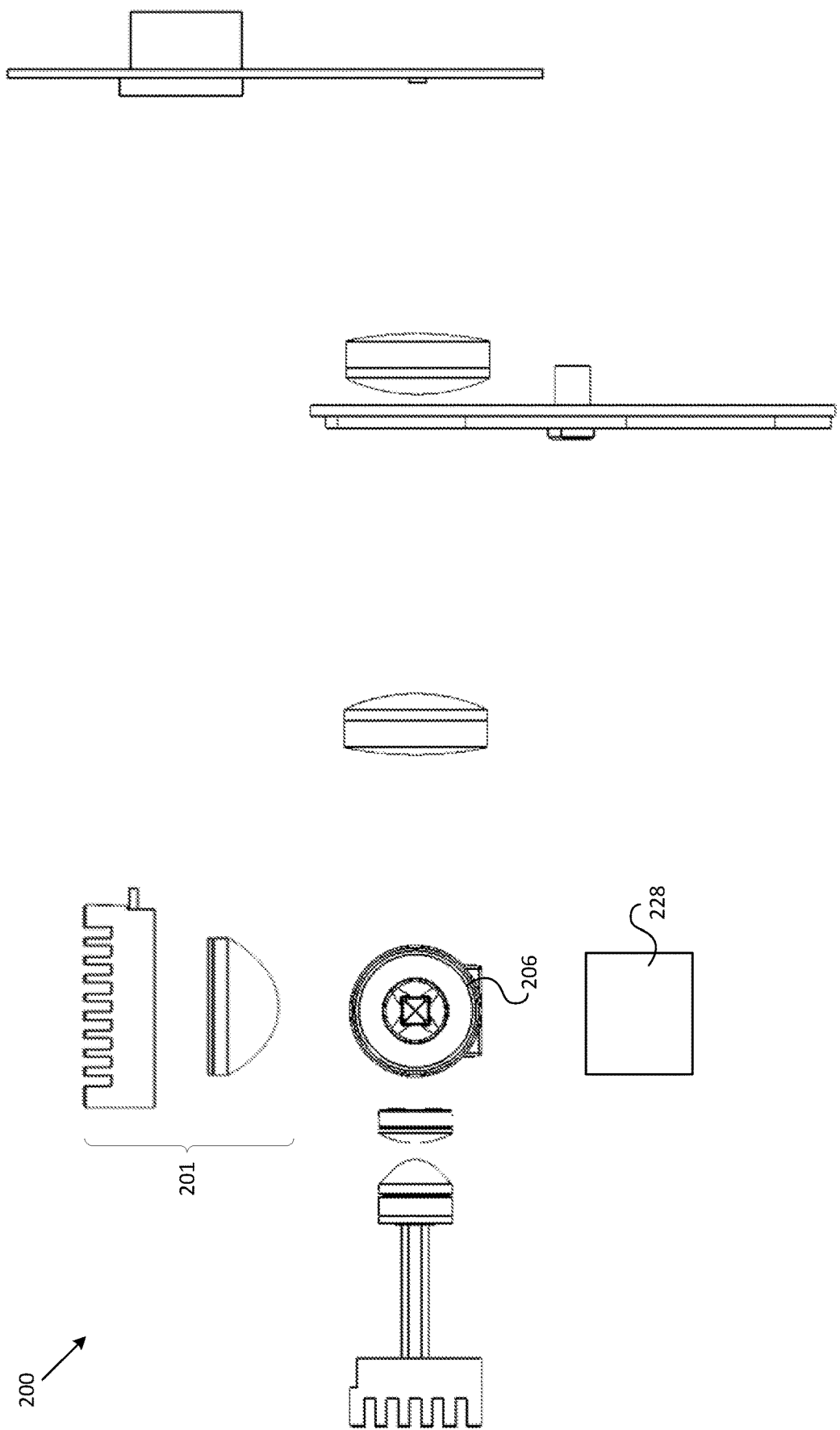
FIG. 2 is an illustration of an isometric view of selected components of an analyzer with an excitation light source positioned orthogonally to a sample cuvette in accordance with an embodiment.

FIG. 2 illustrates selected components of an exemplary analyzer that does not include a dichroic mirror, beam splitter, or piece of non-ultraviolet coated glass. The elements of the analyzer (200) of FIG. 2 are analogous to those of the analyzer (100) of FIGS. 1A-1E. The first light source (201) of analyzer (200) is positioned substantially orthogonal to a sample within a cuvette (206). Because of the location of the first light source (201), it can be used to excite the sample without the need for optical elements such as mirrors, splitters, or lenses to redirect excitation light originating from the light source. It is also appreciated that the first light source (200), as well as each other light source within the analyzer, can alternatively be positioned at any location from which light can be directed to the sample within the cuvette (206). Although it is not depicted in FIG. 2, a sample temperature sensor analogous to the sample temperature sensor (107) of FIGS. 1A-1E can also be present and located at any position from which it can detect the temperature of the sample within the cuvette (206), while not blocking or otherwise interfering with the excitation, emission, or transillumination light beams of the analyzer (200).

Also shown in FIG. 2 is a barcode reader (228). The barcode reader can be used by any of the analyzers described herein to read a barcode present on a face of the cuvette (206). The barcode of the cuvette (206) can, for example, be a one-dimensional or a two-dimensional barcode. The barcode can communicate information about the contents of a sample or reagents within the cuvette (206). Such information can identify, for example, the patient from which a sample originated; one or more individuals, laboratories, or other facilities involved in the handling or processing of the sample; lot numbers or chemistry types of materials within the cuvette; or information related to one or more assay types to be carried out with the sample using the analyzer. The barcode reader (228) can be any imager or detector known within the art to be capable of scanning, reading, detecting, or photographing barcodes. In some embodiments, the barcode reader (228) comprises a complementary metal-oxide-semiconductor (CMOS) camera. The barcode reader (228) can be located at any position from which it can detect the barcode on the cuvette (206) while not blocking or otherwise interfering with the excitation, emission, or transillumination light beams of the analyzer (200).

Figure 3:
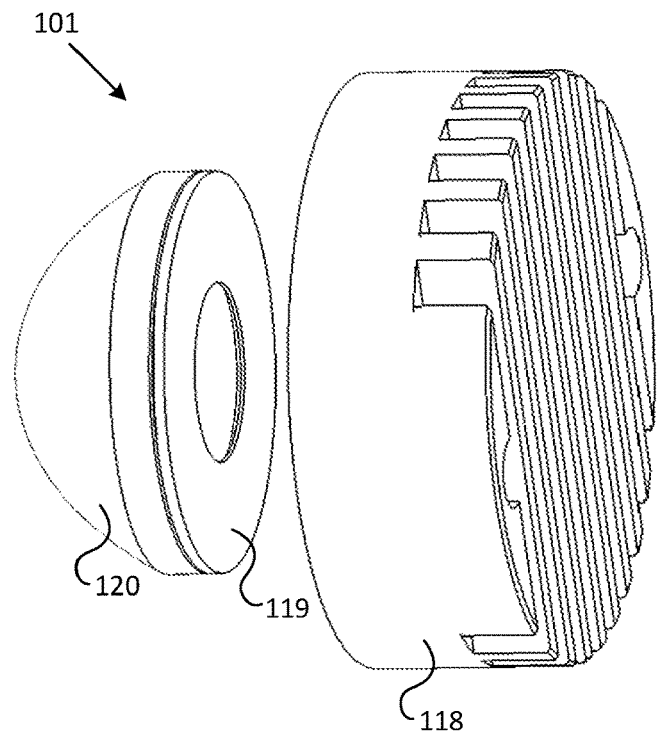
FIG. 3 is an illustration of selected components of the first light source of the analyzer of FIG. 1A.

FIG. 3 illustrates selected components of the first light source (101) of the analyzer (100) of FIGS. 1A and 1B. The first light source (101) can include a housing or cap (118) with ribs to dissipate heat, which can include one or more light emitting diodes (LED). In some embodiments, the first light source (101) includes two or more LED lights. In some embodiments, the first light source (101) includes an LED light configured to produce ultraviolet light. Also shown in FIG. 2 is an aperture (119), and a lens (120). The lens (120) of the first light source (101) can be a simple lens. The lens (120) can be a compound lens consisting of two or more simple lenses arranged along a common axis. In some embodiments, the lens (120) comprises an aspheric lens. In some embodiments, the lens (120) comprises a collimating lens. An example of a lens (120) suitable for use with the first light source (101) is aspheric lens ACL2520U, commercially available from Thorlabs (Newton, N.J.). Those of skill in the art will know of other lenses that are suitable for uses described herein.

It is appreciated the first light source can alternatively include one or more means other than LEDs for emitting light. Such alternative light sources can include, for example, one or more photodiodes, phosphorescent light sources, photomultiplier tubes, arc xenon lamps, incandescent xenon lamps, pulsed xenon lamps, high-pressure mercury lamps, xenon-mercury arc lamps, quartz-tungsten halogen lamps, low pressure mercury lamps, low pressure mercury-argon lamps, hydrogen-deuterium lamps, xenon flash lamps, lasers or combinations thereof. Those of skill in the art will know of other light sources that are suitable for uses described herein.

The first light source can include further optical systems for altering the properties and directions of light being produced. Elements of such optical systems can include, for example, one or more lenses, filters, apertures, diffusers, mirrors, beam splitter, or windows. In general, the second light source includes elements used to diffuse and collimate the excitation light before the excitation light passes through the sample.

The excitation light generated by the first light source can have a wavelength ranging, for example, from 200 nm to 500 nm, e.g., from 200 nm to 380 nm, from 230 nm to 410 nm, from 260 nm to 440 nm, from 290 nm to 470 nm, or from 320 nm to 500 nm. The excitation light can have a wavelength ranging from 330 nm to 380 nm, e.g., from 330 nm to 360 nm, from 335 nm to 365 nm, from 340 nm to 370 nm, from 345 nm to 375 nm, or from 350 nm to 380 nm. In terms of upper limits, the excitation wavelength can be less than 500 nm, e.g., less than 470 nm, less than 440 nm, less than 410 nm, less than 380 nm, less than 350 nm, less than 320 nm, less than 290 nm, less than 260 nm, or less than 230 nm. In terms of lower limits, the excitation wavelength can be greater than 200 nm, e.g., greater than 230 nm, greater than 260 nm, greater than 290 nm, greater than 320 nm, greater than 350 nm, greater than 380 nm, greater than 410 nm, greater than 440 nm, or greater than 470 nm. In some embodiments, the excitation light has a wavelength within the ultraviolet wavelength range, e.g., from 100 nm to 400 nm.

In some embodiments, and as is shown in FIGS. 1A-1E, the analyzer (100) includes an excitation objective lens (108) positioned between the dichroic mirror (105) and the sample contained within the cuvette (106). As excitation light (113) from the first light source (101) is reflected off the dichroic mirror (105), this light (113) passes through the excitation objective lens (108), which can act to focus the excitation light (114) onto the sample. In some embodiments, the excitation objective lens (108) focuses the excitation light (114) through an optical window of a cuvette (106) holding the sample. The excitation objective lens (108) can be a simple lens. The excitation objective lens (108) can be a compound lens comprising two or more simple lenses arranged along a common axis. In some embodiments, the excitation objective lens (108) comprises an aspheric lens. In some embodiments, the excitation objective lens (108) comprises a collimating lens.

Figure 4:
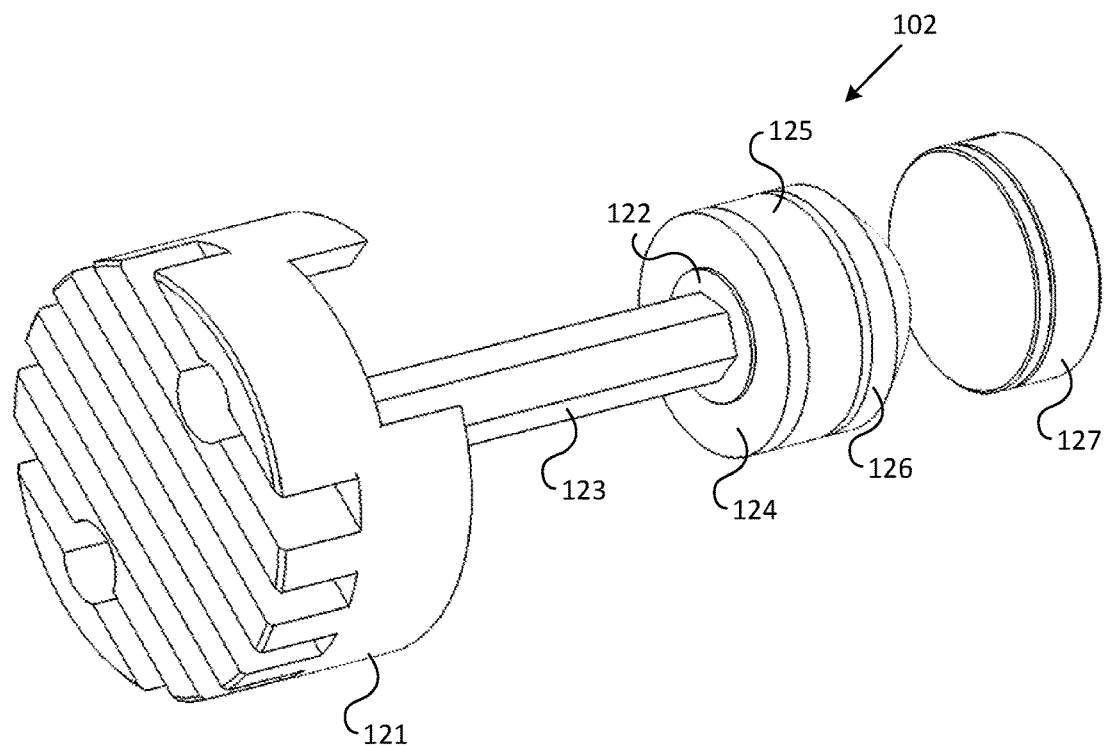
FIG. 4 is an illustration of selected components of the second light source of the analyzer of FIG. 1A.

FIG. 4 illustrates selected components of the second light source (102) of the analyzer (100) of FIGS. 1A and 1B. The second light source can include a housing or cap (121) with ribs to dissipate heat, which can include one or more LED lights. In some embodiments, the second light source (102) includes two or more (e.g., three, four, or more than four) LED lights. In certain aspects, each one of the two or more LED lights is configured to emit light having a different wavelength than that emitted from the other of the two or more LED lights. In some embodiments, the second light source (102) includes a first LED light configured to emit visible red light, and a second LED light configured to emit visible green light. In some aspects the red and green emitting diodes provided different sensitivities and/or absorbance responses when used to analyze different samples. For example, in some instances the green transillumination light can produce a more linear absorbance response for samples with absorbance values below 4, and the red transillumination light can provide a more linear response for samples with absorbance values above 4. In certain aspects, each of more than two LED lights of the second light source (102) has a different dominant wavelength than that of the other of the more than two LED lights of the second light source. As used herein, the term "dominant wavelength" refers to the most frequent wavelength of photons emitted from a light source (e.g., a light emitting diode). In some embodiments, the second light source (102) includes four LED lights, each emitting light having a different wavelength than that emitted by the other of the four LED lights. The inclusion of multiple LED types within the second light source can increase the robustness and flexibility of the analyzer in use with varied assay methods and materials.

The second light source can emit light outside of the visible spectrum, e.g., light having a wavelength below 390 nm, below 380 nm, below 370 nm, below 360 nm, below 350 nm, below 340 nm, below 330 nm, below 320 nm, below 310 nm, below 300 nm, below 290 nm, or below 280 nm. The second light source can include one LED light, two LED lights, three LED lights, four LED lights, or more than four LED lights. Each LED light of the second light source can emit light of a different wavelength, or light of a similar or identical wavelength to that of light emitted by another second light source LED light. It is appreciated the second light source can alternatively include one or more means other than LEDs for emitting light. Such alternative light sources can include, for example, one or more photodiodes, phosphorescent light sources, photomultiplier tubes, arc xenon lamps, incandescent xenon lamps, pulsed xenon lamps, high-pressure mercury lamps, xenon-mercury arc lamps, quartz-tungsten halogen lamps, low pressure mercury lamps, low pressure mercury-argon lamps, hydrogen-deuterium lamps, xenon flash lamps, or lasers. Those of skill in the art will know of other light sources that are suitable for uses described herein.

Also shown in FIG. 4 is a diffuser (122) and a light pipe (123) connecting the second light source housing (121) to the diffuser (122). The diffuser can be used to overcome the positional displacement of the one or more LEDs or other light emitting means. This can work to mitigate, for example, beam deflection due to LEDs being positioned outside of the optical path of the second light source. The light pipe can be used to transfer light from the LED lights to the diffuser. In some embodiments, and as is shown in FIG. 4, the light pipe has a hexagonal cross section. The light pipe can include reflective material or one or more optical fibers. The second light source also includes a first aperture (124) and a second aperture (125), wherein the first aperture (124) is smaller than the second aperture (125). The second light source also includes a first lens (126) adjacent to the second aperture (125), and a second lens (127) separated from the first lens (126) by an air gap. The first (126) and second (127) lenses of the second light source (102) can each independently be a simple lens. The first (126) and second (127) lenses can each independently be a compound lens consisting of two or more simple lenses arranged along a common axis. In some embodiments, the first (126) and second (127) lenses each independently comprise an aspheric lens. In some embodiments, the first (126) and second (127) lenses each independently comprise a collimating lens. An example of a first lens (126) suitable for use with the second light source (102) is aspheric lens ACL2520U, commercially available from Thorlabs. An example of a second lens (127) suitable for use with the second light source (102) is achromatic lens ACL1270, commercially available from Phosctech (Fujian, China).

The second light source can include further optical systems for altering the properties and directions of light being produced. Elements of such optical systems can include, for example, one or more lenses, filters, apertures, diffusers, mirrors, beam splitter, or windows. In general, the second light source includes elements used to diffuse and collimate the transillumination light before the transillumination light passes through the sample.

The transillumination light generated by the first light source can have a wavelength ranging, for example, from 400 nm to 700 nm, e.g., from 400 nm to 580 nm, from 430 nm to 610 nm, from 460 nm to 640 nm, from 490 nm to 670 nm, or from 520 nm to 700 nm. In terms of upper limits, the transillumination wavelength can be less than 700 nm, e.g., less than 670 nm, less than 640 nm, less than 610 nm, less than 580 nm, less than 550 nm, less than 520 nm, less than 490 nm, less than 460 nm, or less than 430 nm. In terms of lower limits, the transillumination wavelength can be greater than 400 nm, e.g., greater than 430 nm, greater than 460 nm, greater than 490 nm, greater than 520 nm, greater than 550 nm, greater than 580 nm, greater than 610 nm, greater than 640 nm, or greater than 670 nm. In some embodiments, the transillumination light has a wavelength within the visible light range, e.g., from 390 nm to 700 nm.

The emission light generated by the sample can have a wavelength ranging, for example, from 400 nm to 700 nm, e.g., from 400 nm to 580 nm, from 430 nm to 610 nm, from 460 nm to 640 nm, from 490 nm to 670 nm, or from 520 nm to 700 nm. In terms of upper limits, the emission wavelength can be less than 700 nm, e.g., less than 670 nm, less than 640 nm, less than 610 nm, less than 580 nm, less than 550 nm, less than 520 nm, less than 490 nm, less than 460 nm, or less than 430 nm. In terms of lower limits, the emission wavelength can be greater than 400 nm, e.g., greater than 430 nm, greater than 460 nm, greater than 490 nm, greater than 520 nm, greater than 550 nm, greater than 580 nm, greater than 610 nm, greater than 640 nm, or greater than 670 nm. In some embodiments, the emission light has a wavelength within the visible light range, e.g., from 390 nm to 700 nm.

In some embodiments, the first light detector includes a photodiode. In some embodiments, the first light detector is a photodiode. The first light detector can be a silicon photodiode. The first light detector can include additional optical elements including one or more filters or lenses. The electronic response of the first light detector can vary with temperature. In some embodiments, the analyzer includes one or more excitation temperature sensors configured to detect the temperature of the first light detector. The excitation temperature sensor can include, for example, a thermocouple, a resistive temperature detector (RTD), a thermistor, or a thermostat. The one or more excitation temperature sensors can detect the temperature of the first light detector at one location or at multiple locations.

The second light detector can be selected for properties that include, for example, high gain, low voltage, fast response, and compact size. In some embodiments, the second light detector includes a silicon photomultiplier detector. In some embodiments, the second light detector is a silicon photomultiplier detector. The second light detector can include additional optical elements including one or more filters or lenses. The electronic response of the first light detector can vary with temperature. In some embodiments, the analyzer includes one or more emission temperature sensors configured to detect the temperature of the second light detector. The emission temperature sensor can include, for example, a thermocouple, a resistive temperature detector (RTD), a thermistor, or a thermostat. The one or more emission temperature sensors can detect the temperature of the second light detector at one location or at multiple locations.

In some embodiments, the dichroic mirror of the analyzer is configured at substantially a 45-degree angle relative to a line connecting the sample and a portion of the first light source. The dichroic mirror can be positioned to have a substantially 45-degree angle of incidence relative to the excitation light beam produced by the first light source. As used herein, the term "substantially" is used to modify a stated angle measurement to indicate that an actual angle measurement can range from 10 degrees less than the stated angle to 10 degrees more than the stated angle, e.g., from 9 degrees less than the stated angle to 9 degrees more than the stated angle, from 8 degrees less than the stated angle to 8 degrees more than the stated angle, from 7 degrees less than the stated angle to 7 degrees more than the stated angle, from 6 degrees less than the stated angle to 6 degrees more than the stated angle, from 5 degrees less than the stated angle to 5 degrees more than the stated angle, from 4 degrees less than the stated angle to 4 degrees more than the stated angle, from 3 degrees less than the stated angle to 3 degrees more than the stated angle, from 2 degrees less than the stated angle to 2 degrees more than the stated angle, or from 1 degree less than the stated angle to 1 degree more than the stated angle. For example, the dichroic mirror angle relative to a line connecting the sample and a portion of the first light source can range from 35 degrees to 55 degrees, e.g., from 36 degrees to 54 degrees, from 37 degrees to 53 degrees, from 38 degrees to 52 degrees, from 39 degrees to 51 degrees, from 40 degrees to 50 degrees, from 41 degrees to 49 degrees, from 42 degrees to 48 degrees, from 43 degrees to 47 degrees, or from 44 degrees to 46 degrees.

In exemplary embodiments, the dichroic mirror is positioned to reflect at least a portion of the excitation light from the first light source towards the sample contained in the cuvette. In some embodiments, the dichroic mirror is configured to reflect at least a portion of the excitation light from the first light source at substantially a 90-degree angle. For example, the dichroic mirror can be configured to reflect at least a portion of the excitation from the first light source at an angle ranging from 80 degrees to 100 degrees, from 81 degrees to 99 degrees, from 82 degrees to 98 degrees, from 83 degrees to 97 degrees, from 84 degrees to 96 degrees, from 85 degrees to 95 degrees, from 86 degrees to 94 degrees, from 87 degrees to 93 degrees, from 88 degrees to 92 degrees, or from 89 degrees to 91 degrees.

The dichroic mirror can have a cutoff wavelength ranging, for example, from 200 nm to 500 nm, e.g., from 200 nm to 380 nm, from 230 nm to 410 nm, from 260 nm to 440 nm, from 290 nm to 470 nm, or from 320 nm to 500 nm. The dichroic mirror can have a cutoff wavelength ranging from 350 nm to 400 nm, e.g., from 350 nm to 380 nm, from 355 nm to 385 nm, from 360 nm to 390 nm, from 355 nm to 395 nm, or from 370 nm to 400 nm. In terms of upper limits, the cutoff wavelength can be less than 500 nm, e.g., less than 470 nm, less than 440 nm, less than 410 nm, less than 380 nm, less than 350 nm, less than 320 nm, less than 290 nm, less than 260 nm, or less than 230 nm. In terms of lower limits, the cutoff wavelength can be greater than 200 nm, e.g., greater than 230 nm, greater than 260 nm, greater than 290 nm, greater than 320 nm, greater than 350 nm, greater than 380 nm, greater than 410 nm, greater than 440 nm, or greater than 470 nm.

The percentage of excitation light reflected by the dichroic mirror can range, for example, from 75% to 100%, e.g., from 75% to 90%, from 77.5% to 92.5%, from 80% to 95%, from 82.5% to 97.5%, or from 85% to 100%. In terms of upper limits, the percentage of excitation light reflected by the dichroic mirror can be less than 100%, e.g., less than 97.5%, less than 95%, less than 92.5%, less than 90%, less than 87.5%, less than 85%, less than 82.5%, less than 80%, or less than 77.5%. In terms of lower limits, the percentage of excitation light reflected by the dichroic mirror can be greater than 75%, e.g., greater than 77.5%, greater than 80%, greater than 82.5%, greater than 85%, greater than 87.5%, greater than 90%, greater than 92.5%, greater than 95%, or greater than 97.5%.

The percentage of excitation light transmitted by the dichroic mirror can range, for example, from 0% to 25%, e.g., from 0% to 15%, from 2.5% to 17.5%, from 5% to 20%, from 7.5% to 22.5%, or from 10% to 25%. In terms of upper limits, the percentage of excitation light transmitted by the dichroic mirror can be less than 25%, e.g., less than 22.5%, less than 20%, less than 17.5%, less than 15%, less than 12.5%, less than 10%, less than 7.5%, less than 5%, or less than 2.5%. In terms of lower limits, the percentage of excitation light transmitted by the dichroic mirror can be greater than 0%, e.g., greater than 2.5%, greater than 5%, greater than 7.5%, greater than 10%, greater than 12.5%, greater than 15%, greater than 17.5%, greater than 20%, or greater than 22.5%.

The sample can be any material or composition to be analyzed. In some embodiments, the sample comprises a liquid composition. In some embodiments, the sample consists of a single liquid component. In some embodiments, the sample is a mixture that includes one or more analytes of interest. The sample can include any biological specimen or sample obtained from a subject. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), a tissue sample (e.g., tumor tissue) such as a surgical resection of a tumor, and cellular extracts thereof. In some embodiments, the sample is whole blood or a fractional component thereof such as plasma, serum, or a cell pellet.

As used herein, "subject" refers to animals such as mammals, including, but not limited to, primates (e.g., humans), cows, sheep, goats, horses, dogs, cats, rabbits, rats, mice and the like. In certain embodiments, the subject is a human.

As used herein, the term "analyte" refers to any molecule, compound, or complex of interest, whose presence, amount, expression level, activation state, and/or identity is determined. The determination can be through specific recognition by a binding agent. The molecule, compound, or complex of interest can be a macromolecule such as a polypeptide or protein, a polysaccharide, a toxin, a cell wall, a cell capsule, a viral capsule, a viral coat, a flagellum, a fimbria or pilus, a microorganism, a nucleic acid complexed to a protein or a polysaccharide, a lipid, a lipid complexed to a protein or a polysaccharide, a polynucleotide, a polypeptide, a carbohydrate, chemical moiety, or combinations thereof (e.g., phosphorylated or glycosylated polypeptides, etc.).

In some embodiments, and as is shown in FIGS. 1A-1E, the sample is held within a cuvette. The cuvette can be any small-scale container having at least one internal cavity configured to contain a sample. In some embodiments, the cuvette includes optical windows positioned to permit the transmission of the transillumination, excitation, and emission lights of the analyzer as described herein. In some embodiments, the cuvette includes an optical window positioned to permit temperature measurements of the sample with the sample temperature sensor. This optical window can be different from the optical windows used to transmit the transillumination, excitation, and emission lights. In some embodiments, the cuvette is configured to have a shape allowing it to only be inserted into the analyzer in a particular orientation.

In some embodiments, the analyzer includes one or more sample temperature sensors configured to detect the temperature of the sample. The sample temperature sensor can include, for example, a thermocouple, a resistive temperature detector (RTD), a thermistor, or a thermostat. The sample temperature sensor can include an infrared sensor, allowing the sample temperature sensor to measure the temperature at a focused location without requiring any contact of the sensor with the location to be measured. The one or more sample temperature sensors can detect the temperature of the sample at one location or at multiple locations. In some embodiments, the sample temperature sensor measures the temperature at the bottom of the cuvette.

In some embodiments, and as is shown in FIGS. 1A-1E, the analyzer includes one or more band pass filters. The band pass filter can, for example, allow only visible light to pass from the dichroic mirror to the second detector. The band pass filter can be selected or configured, for example, to only pass light having wavelengths ranging from 200 nm to 900 nm or 390 nm to 700 nm, e.g., within the visible light spectrum. It is appreciated that a variety of filters (longpass, shortpass, bandpass, etc.) are known and available to the skilled artisan and can be selected according to the wavelength of light desired for detection.

The band pass filter can be an element of a filter wheel configured to hold multiple band pass filters that can be individually rotated into position between the dichroic mirror and the second light detector. In exemplary embodiments, the filter wheel can include two, three, four, five, six, seven, eight, nine, ten, eleven, twelve, or more than twelve band pass filters.

In some embodiments, the optical and electrical analyzer components described above are contained within an instrument housing. The housing can be configured to minimize leakage of light, dust, particulate matter, or other materials into or out of the instrument interior. The housing can have a combined dimension (i.e., length plus width plus height) that, for example, ranges from 20 inches to 40 inches, e.g., from 20 inches to 32 inches, from 22 inches to 34 inches, from 24 inches to 36 inches, from 26 inches to 38 inches, or from 28 inches to 40 inches. In terms of upper limits, the housing can have a combined dimension that is less than 40 inches, e.g., less than 38 inches, less than 36 inches, less than 34 inches, less than 32 inches, less than 30 inches, less than 28 inches, less than 26 inches, less than 24 inches, or less than 22 inches. In terms of lower limits, the housing can have a combined dimension that is greater than 20 inches, e.g., greater than 22 inches, greater than 24 inches, greater than 26 inches, greater than 28 inches, greater than 30 inches, greater than 32 inches, greater than 34 inches, greater than 36 inches, or greater than 38 inches.

Figure 5A:
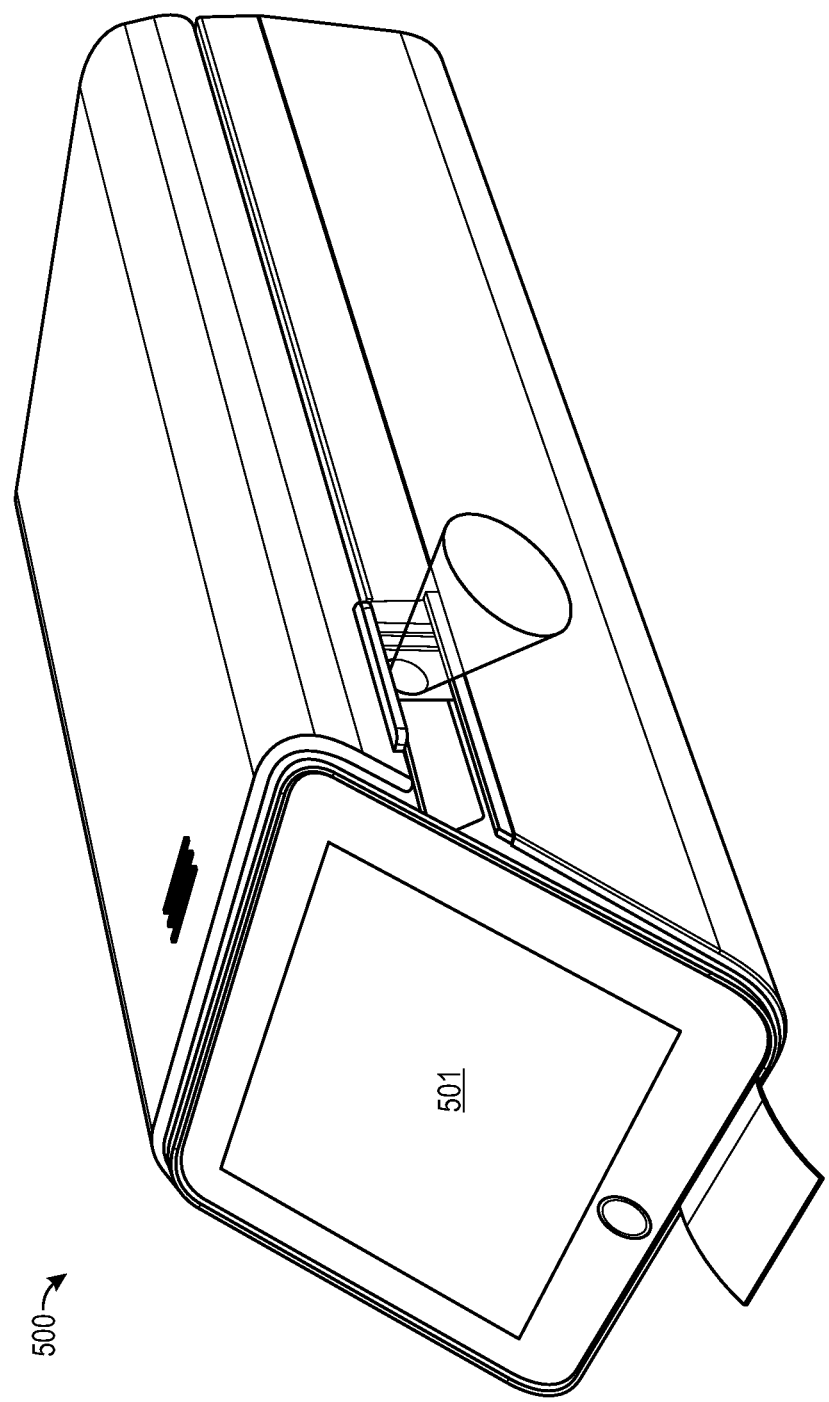
FIG. 5A is an external view of an exemplary analyzer having an instrument housing and a touchscreen in accordance with an embodiment.

FIG. 5A depicts an exemplary analyzer (500) in which the optical and electrical components are contained with an instrument housing as described above. In some embodiments, and as is illustrated in FIG. 5A, the analyzer (500) also includes a touchscreen display (501) that can be used by an operator to input commands or other information related to an assay to be performed by the analyzer (500). The touchscreen (501) can also be used to output assay results, additional data, instructions, or command prompts to the operator. The touchscreen (501) can be mounted onto or within an external surface of the housing.

Commands or other information can be input to the analyzer (500) via the touchscreen (501) in the form of, for example, alphanumeric characters or barcodes. In some embodiments, alphanumeric characters are entered using an on-screen keyboard displayed on the touchscreen (501). In some embodiments, barcodes are entered using a barcode reader. The barcode reader can be an internal component of the analyzer (500), an external component of the analyzer (500), or a piece of equipment separate from, but in communication with, the analyzer (500).

In some embodiments, the touchscreen (501) displays a graphical user interface (GUI) that guides a user in entering information related to a sample to be analyzed, detected or measured. For example, the GUI can display multiple fields for the entry of relevant data. Examples of such data can include, for example, user identification, patient identification, order identification, assay identification, sample identification, or other. The data entry fields can each be accompanied by an on-screen selectable button. The data entry fields can each themselves be on-screen selectable buttons. In some embodiments, the on-screen buttons have an appearance representative of a barcode, indicating that data can currently be entered into the field associated with the button by scanning a barcode with a barcode reader. In some embodiments, when a user pushes the on-screen button having an appearance representative of a barcode, the button appearance toggles to the depiction of an empty field, indicating that data can currently be entered into the field associated with the button by typing with an on-screen keyboard. The appearance of the button, and the method of entering data into the associated field, can thus be toggle back and forth between manual entry or barcode scanning entry as needed. In some embodiments, as data is entered into one field of the GUI, e.g., via barcode scanning, typing, or other means, the next field of the GUI becomes activated, indicating that this field is ready to accept input data.

Figure 5B:
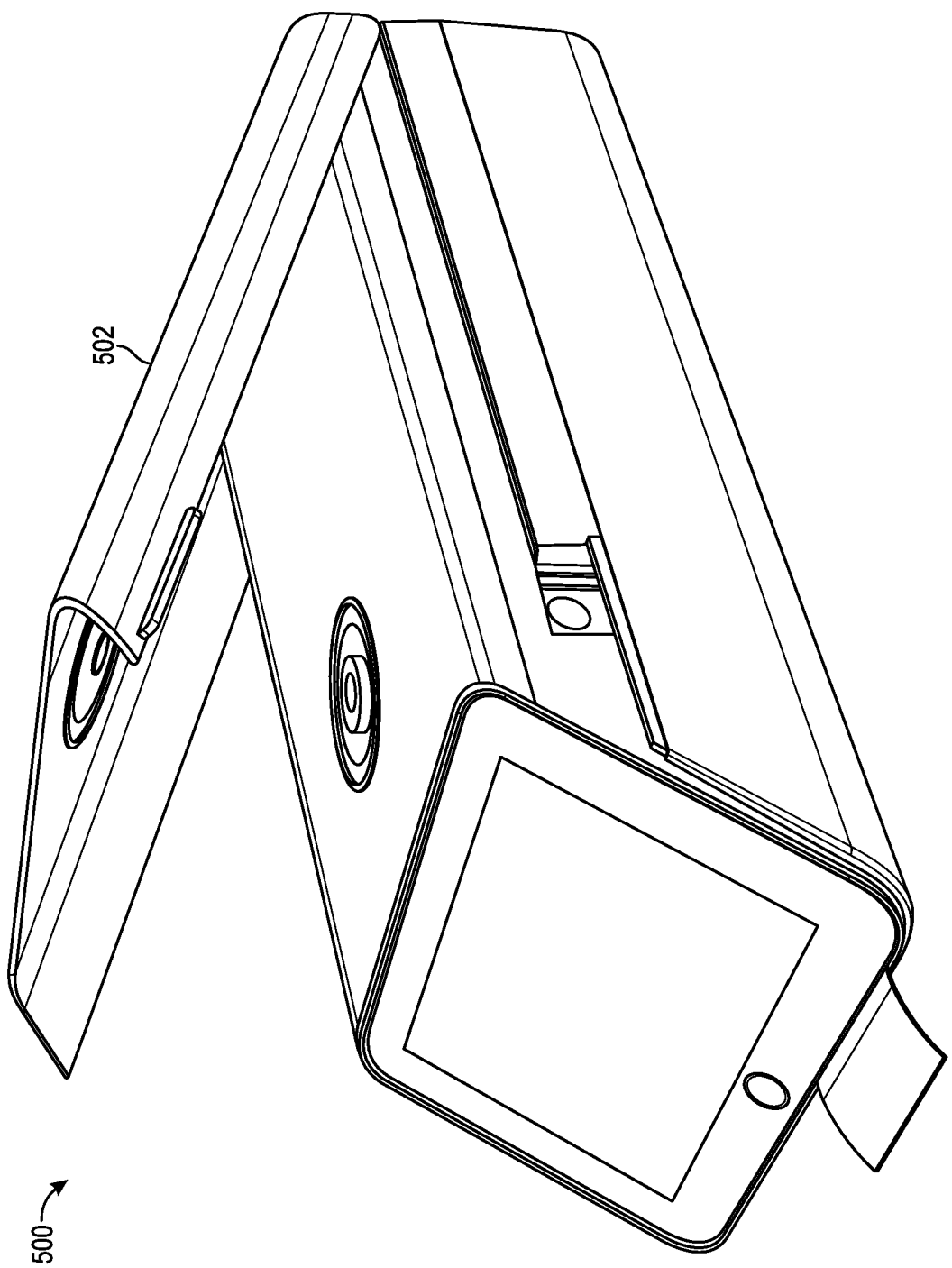
FIG. 5B is an external view of the analyzer of FIG. 5A having a lid in an open configuration.
Figure 5C:
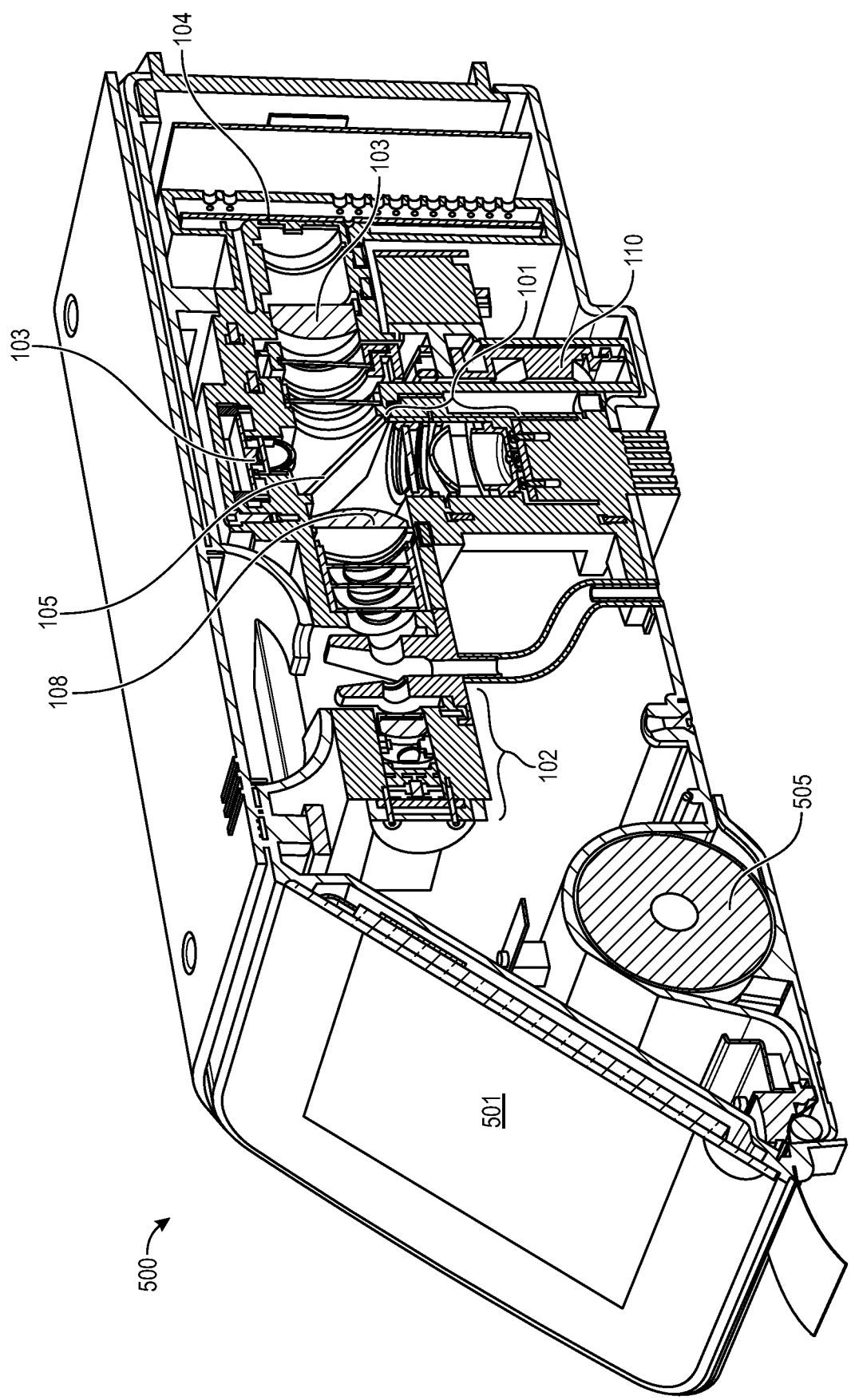
FIG. 5C is a cross-sectional view of the analyzer of FIGS. 5A and 5B having a printer module and internal paper supply.

FIG. 5B depicts the analyzer (500) of FIG. 5A with an associated lid (502) in an open configuration. The lid (502) can be any repositionable covering that can be opened and closed to expose at least a portion of the analyzer interior. The lid (502) can be attached to the analyzer (500) using hinges, bearings, or any other means known and available to the skilled artisan. In some embodiments, the lid (502) is configured to be a break-away lid. In these cases, if the force applied to open the lid (502), e.g. by lifting and/or pushing back on the lid (502), exceeds a particular threshold, then the lid (502) detaches from the analyzer. This break-away lid configuration can reduce the likelihood of the lid (502) from becoming damaged either at a location on the lid (502) itself or at an attachment to the analyzer (500).

FIG. 5C depicts a cross-sectional view of the analyzer (500) of FIGS. 5A and 5B, showing exemplary locations of the optical components as illustrated in FIGS. 1A-1E. In some embodiments, and as is illustrated in FIG. 5C, the analyzer also includes a printer module (503). The printer module (503) can create printed reports (504) by printing onto paper from an internal paper supply (505). The printer module (503) can be located on the same or a different external surface as the touchscreen (501). The use of such a built-in printer module (503) can reduce the introduction of light, dust, or cleaning material into the analyzer housing interior. Such contaminants are more likely to be introduced if a printer is used as an external accessory mounted on the top surface of the analyzer (500).

In some embodiments, the analyzer also includes power supplies configured to provide power to, for example, the light sources, detectors, and sensors of the analyzer. In some embodiments, the analyzer also includes processors and memory configured to store and execute operations related to the functioning of the analyzer. Any one or more of the method steps described herein can be stored and executed using such processors and memory.

In some embodiments, the analyzer has a wired connection to a data display or storage device. The wired connection can include, for example and without limitation, one or more of a serial output port such as an RS-232 or D-sub output port, a Universal Serial Bus (USB) output port, a Digital Visual Interface (DVI) output port, a DisplayPort output port, a Serial AT Attachment (SATA) output port, and a Video Graphics Array (VGA) port. In some embodiments, the analyzer has a wireless connection (e.g., via a WiFi or cellular network) to a data display or storage device. The display device can include a monitor or screen that can be a component of a desktop, laptop, or mobile computing device. The storage device can be a local storage device or a network or "cloud"-based storage device. The analyzer can include a connector configured to couple with a communication port of an external device. In some embodiments, the connector of the analyzer is a serial connector. The serial connector can be, for example and without limitation, an RS-232 connector, an Ethernet connector, a FireWire connector, a USB connector, or an adapter connecter configured to allow compatibility between two different serial connector types.

II. Methods

Figure 6:
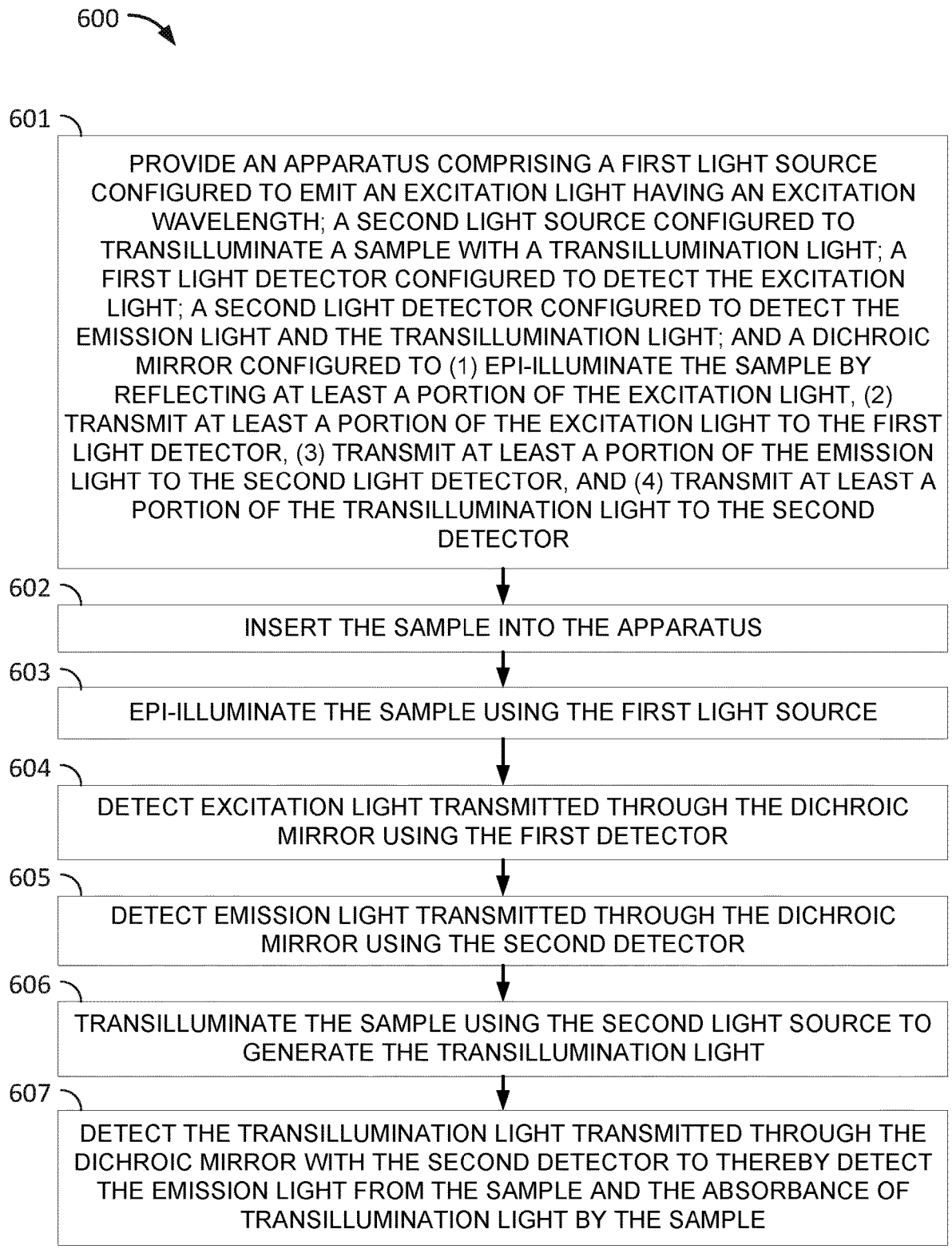
FIG. 6 is a flowchart of a process in accordance with an embodiment.

FIG. 6 presents a flowchart of a method (600) in accordance with an embodiment for detecting an emission light from a sample, and absorbance of transillumination light by the sample. In operation 601, an apparatus is provided, wherein the apparatus comprises a first light source configured to emit an excitation light having an excitation wavelength; a second light source configured to transilluminate the sample with the transillumination light; a first light detector configured to detect the excitation light; a second light detector configured to detect the emission light and the transillumination light; and a dichroic mirror configured to (1) epi-illuminate the sample by reflecting at least a portion of the excitation light, (2) transmit at least a portion of the excitation light to the first light detector, (3) transmit at least a portion of the emission light to the second light detector, and (4) transmit at least a portion of the transillumination light to the second light detector. The apparatus provided in the method can be any of the apparatus as described above.

In operation 602, the sample is inserted into the apparatus. The inserted sample can be any of the samples as described above. In some embodiments, the sample is within a cuvette. In some embodiments, the cuvette is configured to have one or more external surface features configured to fit specifically within a cavity of the apparatus in a particular orientation. This lock-and-key-type configuration can prevent a cuvette from being inserted in a non-functional orientation, or can prevent a non-compliant cuvette from being inserted into the apparatus. In some embodiments, a particular orientation and cuvette design is required to ensure that cuvette features such as optical windows, barcodes, and others are properly aligned with elements within the analyzer allowing the analyzer elements to properly interact with corresponding elements of the cuvette.

In operation 603, the sample is epi-illuminated using the first light source of the apparatus. The epi-illumination can be as shown in FIG. 1C. The epi-illumination can be with excitation light selected according to a particular analytical method. The excitation light can have any of the excitation light properties discussed above.

In operation 604, excitation light transmitted through the dichroic mirror of the apparatus is detected using the first detector. The excitation light transmission can be as shown in FIG. 1C. The intensity of excitation light measured by the first detector provides a value that can be used to correct or otherwise adjust the output power of the first light source. For example, for a given excitation light wavelength and dichroic mirror cutoff wavelength, an expected excitation light transmission intensity can be determined. If the excitation light intensity measured by the first detector is lower than this expected value, then the power of the first light source can be increased accordingly. If the excitation light intensity measured by the first detector is higher than the expected value, then the power of the first light source can be decreased accordingly. The amount by which the light source power is adjusted can be calculated, for example, by applying a function of excitation light intensity in terms of light source power. Such a function can be, for example, derived by regression analysis of data relating excitation light intensity and light source power.

In operation 605, emission light transmitted from the sample through the dichroic mirror of the apparatus is detected using the second detector. In some embodiments, the second detector measures the emission light a single time during each epi-illumination. In some embodiments, the second detector measures the emission light multiple times during each epi-illumination. The second detector can, for example, measure the emission light two times, three times, four time, five times, ten times, fifteen times, twenty times, twenty-five times, thirty times, forty times, fifty times, sixty times, seventy times, eighty times, ninety times, one hundred times, two hundred times, three hundred times, four hundred times, five hundred times, or more than five hundred times during each epi-illumination.

In operation 606, the sample is transilluminated using the second light source to generate the transillumination light. The transillumination can be as shown in FIG. 1D. The transillumination can be with transillumination light selected according to a particular analytical method. The transillumination light can have any of the transillumination light properties discussed above.

In operation 607, the transillumination light transmitted through the dichroic mirror is detected with the second detector, thereby detecting the absorbance of transillumination light by the sample. The absorbance is measured as the attenuation of the transillumination light at its known wavelength. In some embodiments, the second detector measures the transillumination light a single time during each transillumination. In some embodiments, the second detector measures the transillumination light multiple times during each transillumination. The second detector can, for example, measure the transillumination light two times, three times, four time, five times, ten times, fifteen times, twenty times, twenty-five times, thirty times, forty times, fifty times, sixty times, seventy times, eighty times, ninety times, one hundred times, two hundred times, three hundred times, four hundred times, five hundred times, or more than five hundred times during each transillumination.

In some embodiments, after the epi-illuminating of the sample, an inherent fluorescence of the sample is measured using the second detector. Certain components of the sample, such as for example, particular buffers, can have significant inherent fluorescence that can be accounted for when observing further fluorescence measurements. Such inherent, or background fluorescence can cause spurious readings of fluorescence signals unrelated to the assay or analyte of interest. In some embodiments, to compensate and correct for this background effect, the measured inherent fluorescence of one or more sample components is subtracted from the measured fluorescence of the full sample to arrive at a calculated signal representative of the fluorescence contribution of the one or more analytes, analyte complexes, or assay reaction products of interest.

In some embodiments, the apparatus also includes an emission temperature sensor configured to detect the temperature of the second light detector. The temperature detected using the emission temperature sensor can be used to correct a signal output by the second light detector. In some embodiments, the apparatus also includes an excitation temperature sensor configured to detect the temperature of the first light detector. The temperature detected using the excitation temperature sensor can be used to correct a signal output by the first light detector. The correction of signal output to account for sensor temperature can, for example, include applying a mathematical function relating sensor signal output to sensor temperature. The correction can include referencing a look-up table comprising historical reference measurements of sensor signal output at various sensor temperatures.

In some embodiments, prior to inserting the sample into the apparatus, a blank absorbance is measured with the second light detector. The blank absorbance is a measure of the transillumination light intensity arriving at the second light detector as none of the transillumination light is absorbed by a sample. This blank absorbance then provides a control signal value that can be used to subsequently calculate a sample absorbance as the logarithm of the ratio of the control signal to the sample signal. In some embodiments, a blank absorbance is measured with the second light detector after a sample has been removed from the apparatus. The blank absorbance after sample removal can be used to verify that the control signal value has not changed significantly during the time in which the sample was within the analyzer.

In certain aspects, the disclosure embodies devices for calibrating, standardizing or monitoring an analyzer and the optics contained therein. A reference emission device is used to calibrate or standardize the optics, which device is made from a material having known optical emission properties or peaks and comparing the output of the analyzer to an expected output to properly calibrate the analyzer to the reference emission. The material from which the reference device is made can be a fluorescent dye and an acrylic matrix or epoxy.

In one aspect, a fluorescent lanthanide cryptate dye, which is solidified within an acrylic matrix or epoxy in a cuvette is a reference emission device. Cryptate dyes are disclosed for example, in U.S. Pat. Nos. 6,515,113, 6,406,297, and 6,864,103 as well as WO 2015/157057 all of which are incorporated herein by reference. The cryptate solidified within an acrylic matrix or epoxy is structurally strong, durable and has a long-shelf life. Such a device can withstand most any environment in which an analyzer is likely to be employed. The lanthanide cryptate dye solidified within an acrylic or epoxy emits a stable and repeatable reference emission and can be used to calibrate and monitor an analyzer configured to detect optical emissions at many different wavelengths. In various embodiments, the emission is repeatable in the sense that every emission from a particular reference device can be expected to be similar within a relatively small range of variation.

After manufacture, a reference emission device can be checked and characterized before placing into service. For example, a lanthanide cryptate dye has known characteristics emission peaks and these characteristic peaks are confirmed prior to placing it into service. Thereafter, the analyzer can be monitored, standardized or calibrated using a reference emission device. Other known fluorescent compounds can be used in a reference emission device and employed in the analyzer, methods and systems of this disclosure.

In some embodiments, prior to inserting the sample into the apparatus, a dark current is detected with the first and/or second light detector. In some embodiments, prior to the epi-illumination of the sample, a dark current reading is measured with the first and/or second light detector. The dark current reading is a measure of the response of the detector in the absence of the excitation light. The dark current then provides a control signal value that can be used to subsequently correct a signal value obtained in the presence of the excitation light. In some embodiments, a dark current is measured with the first light detector after the epi-illumination of the sample has occurred. The dark current reading after epi-illumination can be used to verify that the dark current has not changed significantly during the time in which the sample was epi-illuminated.

Reference to a "first" component does not necessarily require that a second component be provided. Moreover reference to a "first", "second", or "third" component does not limit the referenced component to a particular location unless expressly stated. The terms "first", "second", and "third" when used herein with reference to elements or properties are simply to more clearly distinguish the two or more elements or properties and unless stated otherwise are not intended to indicate order. As used herein, "a" or "an" means "at least one" or "one or more."

Although the foregoing devices and methods have been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. An apparatus for detecting an emission light from a sample, and absorbance of a transillumination light by the sample, the apparatus comprising:
    a first light source configured to emit an excitation light having an excitation wavelength;
    a second light source configured to transilluminate the sample with the transillumination light;
    a first light detector configured to detect the excitation light;
    a second light detector configured to detect the emission light and the transillumination light; and
    a dichroic mirror configured to (1) epi-illuminate the sample by reflecting at least a portion of the excitation light, (2) transmit at least a portion of the excitation light to the first light detector, (3) transmit the emission light to the second light detector, and (4) transmit the transillumination light not absorbed by the sample to the second light detector.

2. The apparatus of claim 1, further comprising:
    an emission temperature sensor configured to detect the temperature of the second light detector.

3. The apparatus of claim 1, further comprising:
    an excitation temperature sensor configured to detect the temperature of the first light detector.

4. The apparatus of claim 1, further comprising:
    a sample temperature sensor configured to detect the temperature of the sample.

5. The apparatus of claim 4, wherein the sample temperature sensor is located substantially orthogonal to a line comprising the sample and a portion of the dichroic mirror.

6. The apparatus of claim 1, wherein the dichroic mirror is configured at substantially a 45-degree angle relative to a line comprising the sample and a portion of the first light source.

7. The apparatus of claim 6, wherein the dichroic mirror is configured to reflect at least a portion of the excitation light from the first light source at substantially a 90-degree angle.

8. The apparatus of claim 1, further comprising an excitation objective lens between the dichroic mirror and the sample.

9. The apparatus of claim 8, wherein the excitation objective lens is configured to focus the excitation light onto the sample.

10. The apparatus of claim 1, further comprising:
    a band pass filter disposed between the second light detector and the dichroic mirror.

11. The apparatus of claim 10, wherein the band pass filter allows only visible light having a wavelength ranging from 390 nm to 700 nm to pass to the second light detector.

12. The apparatus of claim 10, wherein the emission light transmitted through the dichroic mirror passes through the band pass filter and is focused on the second light detector.

13. The apparatus of claim 10, wherein the transillumination light transmitted through the dichroic mirror passes through the band pass filter and is focused on the second light detector.

14. The apparatus of claim 10, further comprising:
a filter wheel holding the band pass filter.

15. The apparatus of claim 14, wherein the band pass is a first band pass filter, and wherein the filter wheel further holds one or more additional band pass filters.

16. The apparatus of claim 1, wherein the second light detector is a silicon photomultiplier detector.

17. The apparatus of claim 1, wherein the first light detector is a photodiode.

18. The apparatus of claim 1, wherein the excitation light has a wavelength within the ultraviolet wavelength range.

19. The apparatus of claim 1, wherein the transillumination light has a wavelength within the visible wavelength range.

20. The apparatus of claim 1, wherein the second light source comprises a first light emitting diode (LED) configured to emit a first light, and a second LED configured to emit a second light.

21. The apparatus of claim 1, wherein the second light source comprises more than two light emitting diodes.

22. The apparatus of claim 21, wherein each one of the more than two light emitting diodes has a dominant emission wavelength that is different from the dominant emission wavelength of the other of the more than two light emitting diodes.

23. The apparatus of claim 1, further comprising:
a cuvette holding the sample.

24. The apparatus of claim 1, further comprising:
an instrument housing, wherein the first light source the second light source, the first light detector, the second light detector, and the dichroic mirror are each within the instrument housing.

25. The apparatus of claim 24, further comprising:
a barcode reader.

26. The apparatus of claim 25, wherein the barcode reader is within the instrument housing.

27. The apparatus of claim 25, wherein the barcode reader is external to the instrument housing.

28. The apparatus of claim 24, further comprising:
a printer module within the instrument housing.

29. The apparatus of claim 24, further comprising:
a touchscreen mounted to an external surface of the housing.

30. The apparatus of claim 1, wherein at least one of the first light source and the second light source comprises a cap with ribs configured to dissipate heat.

31. The apparatus of claim 1, wherein the sample comprises whole blood, plasma, serum, red blood cells, or white blood cells.

32. A method for detecting an emission light from a sample, and absorbance of transillumination light by the sample, the method comprising:
providing the apparatus of claim 1;
inserting the sample into the apparatus;
epi-illuminating the sample using the first light source;
detecting excitation light transmitted through the dichroic mirror using the first detector;
detecting emission light transmitted from the sample through the dichroic mirror using the second detector;
transilluminating the sample using the second light source to generate the transillumination light; and
detecting the transillumination light transmitted through the dichroic mirror with the second detector to thereby detect the absorbance of transillumination light by the sample.

33. A system for detecting an emission light from a sample, and absorbance of transillumination light by the sample, the system comprising:
the apparatus of claim 1;
at least one processor; and
a memory operatively coupled with the at least one processor.

\* \* \* \* \*